United States Patent [19]

Rosen et al.

[11] Patent Number: 5,532,394

[45] Date of Patent: Jul. 2, 1996

[54] ADDITION POLYMERIZATION CATALYSTS COMPRISING REDUCED OXIDATION STATE METAL COMPLEXES

[75] Inventors: Robert K. Rosen, Sugar Land, Tex.; Peter N. Nickias, Midland, Mich.; David D. Devore, Midland, Mich.; James C. Stevens, Midland, Mich.; Francis J. Timmers, Midland, Mich.

[73] Assignee: The Dow Chemical Company, Midland, Mich.

[21] Appl. No.: 295,768

[22] PCT Filed: Mar. 19, 1993

[86] PCT No.: PCT/US93/02584

§ 371 Date: Sep. 2, 1994

§ 102(e) Date: Sep. 2, 1994

[87] PCT Pub. No.: WO93/19104

PCT Pub. Date: Sep. 30, 1993

Related U.S. Application Data

[60] Division of Ser. No. 8,003, Jan. 21, 1993, Pat. No. 5,374,696, which is a continuation-in-part of Ser. No. 941,014, Sep. 4, 1992, abandoned, which is a continuation-in-part of Ser. No. 857,886, Mar. 26, 1992, abandoned.

[51] Int. Cl.$^6$ .................................................. C07F 17/00
[52] U.S. Cl. .................................. 556/11; 556/13; 556/19; 556/52; 556/7; 502/155; 526/126; 526/170; 526/10
[58] Field of Search ........................... 556/11, 13, 20, 556/21, 53, 7, 10, 19

[56] References Cited

U.S. PATENT DOCUMENTS 4,057,565  11/1977  Manzer ........................... 250/429 R
4,870,042  9/1989  Kohara et al. ........................ 502/114
5,064,802  11/1991  Stevens et al. ....................... 502/155
5,189,192  2/1993  LaPointe et al. ..................... 556/11

FOREIGN PATENT DOCUMENTS 416815  3/1991  European Pat. Off. .

OTHER PUBLICATIONS

J. Am. Chem. Soc. 113, 3623–3625 (1991).

Organometallics 10, 3227–3237 (1991).

Primary Examiner—David W. Wu

[57] ABSTRACT

Metal complexes useful in the formation of addition polymerization catalysts of the formula:

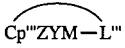

wherein Cp''' is a cyclopentadienyl group or substituted derivative thereof;

Z is a divalent moiety comprising oxygen, nitrogen, phosphorous, boron or a member of Group 4 of the Periodic Table of Elements;

Y is a linking group comprising nitrogen, phosphorus, oxygen or sulfur;

M is a Group 4 metal in the +3 oxidation state; and

L''' is a monovalent anionic stabilizing ligand.

5 Claims, 3 Drawing Sheets

ADDITION POLYMERIZATION CATALYSTS COMPRISING REDUCED OXIDATION STATE METAL COMPLEXES

This is a divisional application of U.S. Ser. No. 08/008,003, filed Jan. 21, 1993, now U.S. Pat. No. 5,374,696, which is a continuation-in-part of U.S. Ser. No. 07/941,014 filed Sep. 4, 1992, now abandoned, which is a continuation-in-part of U.S. Ser. No. 07/857,886, filed Mar. 26, 1992 now abandoned.

This invention relates to addition polymerization catalysts comprising certain stabilized, reduced metal complexes. In one embodiment such catalysts additionally employ an activating cocatalyst. In another embodiment such catalysts may be employed with or without an activating cocatalyst. Finally the invention relates to an improved method for preparing the stabilized reduced metal complexes. The compositions are especially useful as catalysts for the polymerization of olefins such as ethylene for the preparation of polymers having utility as molding resins and in the formation of foamed products having cushioning and insulating applications and films that are useful as protective wrappings.

In U.S. Ser. No. 545,403, filed Jul. 3, 1990 (equivalent to EP-A-0416,845)there are disclosed and claimed certain monocyclopentadienyl metal complexes having utility as homogeneous olefin polymerization catalysts. In U.S. Pat. No. 5,064,802 (equivalent to EP-A-0418,044), cationic monocyclopentadienyl metal complexes with salts of Bronsted acids containing a non-coordinating compatible anion are disclosed and claimed. In U.S. Ser. No. 547,718, also filed on Jul. 3, 1990 now abandoned (EP-A-0468,651), an oxidative activation technique for preparing such cationic catalysts is disclosed and claimed.

In U.S. Pat. No. 4,057,565 there are disclosed Ti, Zr, or Hf derivatives of 2-dialkylaminobenzyl or 2-dialkylaminomethylphenyl all in the +4 oxidation state which are useful as components of catalysts for olefin polymerization.

In *J. Am. Chem. Soc.* 100, 8068–8073 (1978) there is mentioned the synthesis and characterization of Ti(+3) complexes containing cyclopentadienyl groups and 2-dialkylaminobenzyl or 2-dialkylaminomethylphenyl groups. No mention of utility as addition polymerization catalysts is given.

In U.S. Pat. No. 4,870,042, catalysts for olefin polymerizations comprising a pyrazolyl borate complex of titanium or zirconium compounds including titanium trichloride (Example 4) are disclosed.

In *Organometallics;* 10,3227–3237(1991) certain titanium+3 complexes containing cyclopentadienyl groups and alkyl groups are mentioned. On page 3236, the reference states:

"So far no well-defined neutral titanium-based molecular system with established activity for catalytic olefin polymerization has been described.... Apparently, the tervalent Cp*$_2$TiR system cannot induce sufficient positive charge at the β-carbon atom of an incoming ethylene molecule to reach the polar transition state for migratory insertion."

In *Journal of Organometallic Chemistry,* 334 (1987) C1–C4, $\eta^3$-allyl(bis-$\eta^5$-cyclopentadienyl)titanium (III) activated with dimethylaluminum chloride was found to create a coordinated species Cp$_2$Ti(allyl)-(CH$_3$)$_2$AlCl which was found to polymerize ethylene to a small extent. Use of stronger Lewis acids so as to cause ligand abstraction thereby destroying the requisite carbon-titanium bond was to be avoided according to the reference.

Figure 1:
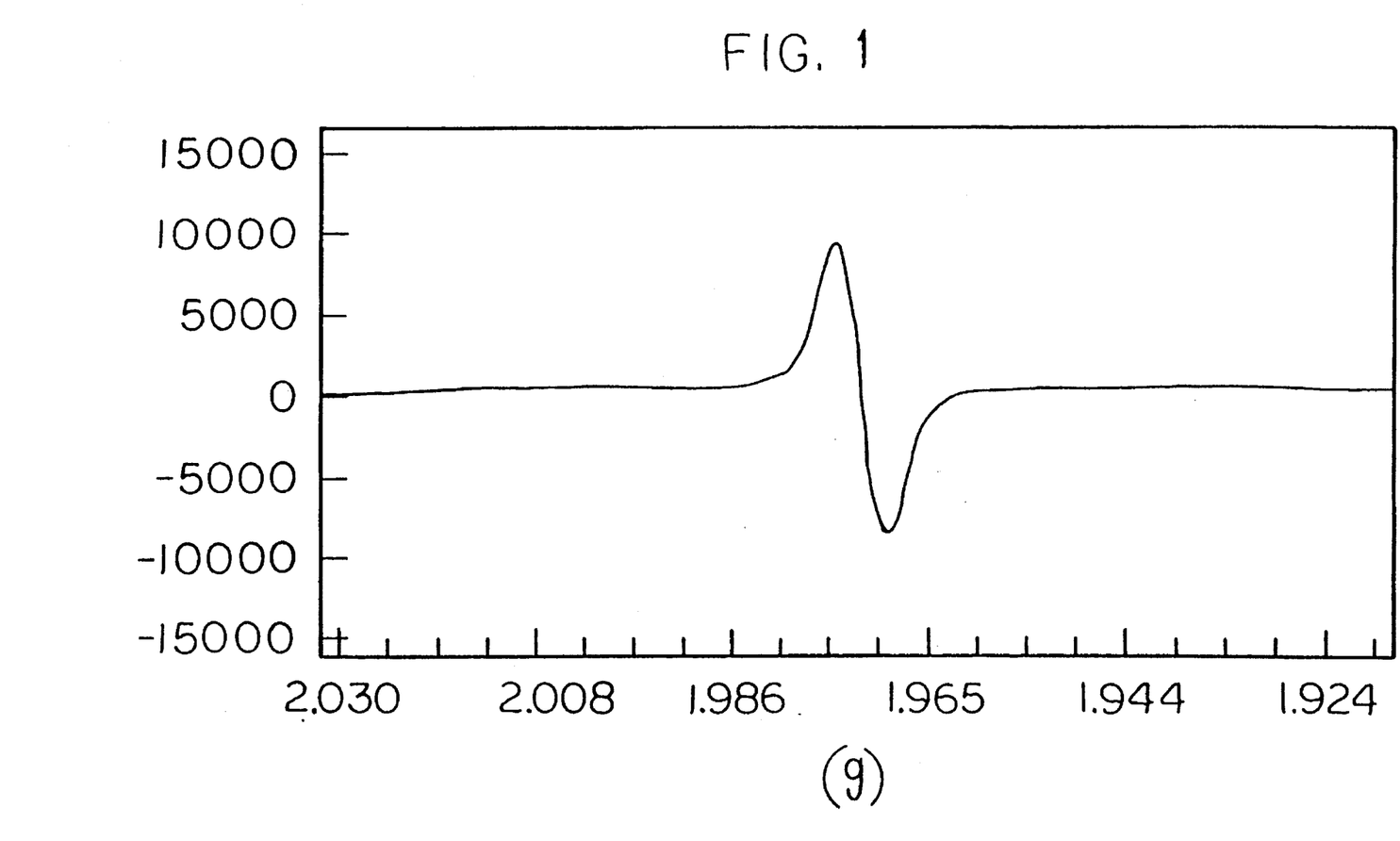
FIG. 1 is an electron spin resonance spectrogram of the product obtained in preparation ii) of Examples 1–58.
Figure 2:
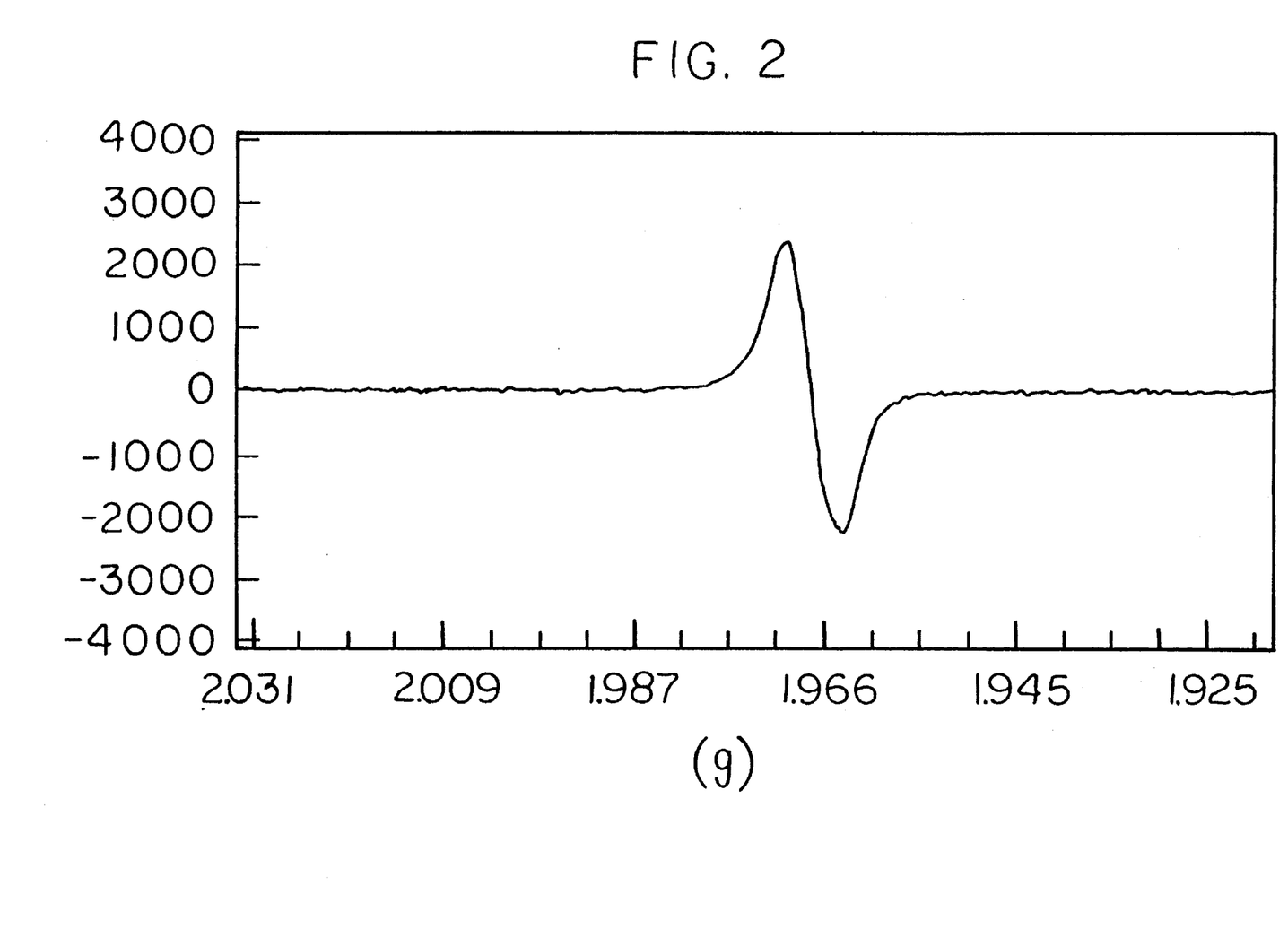
FIG. 2 is an electron spin resonance spectrogram of the product obtained in Example 59.
Figure 3:
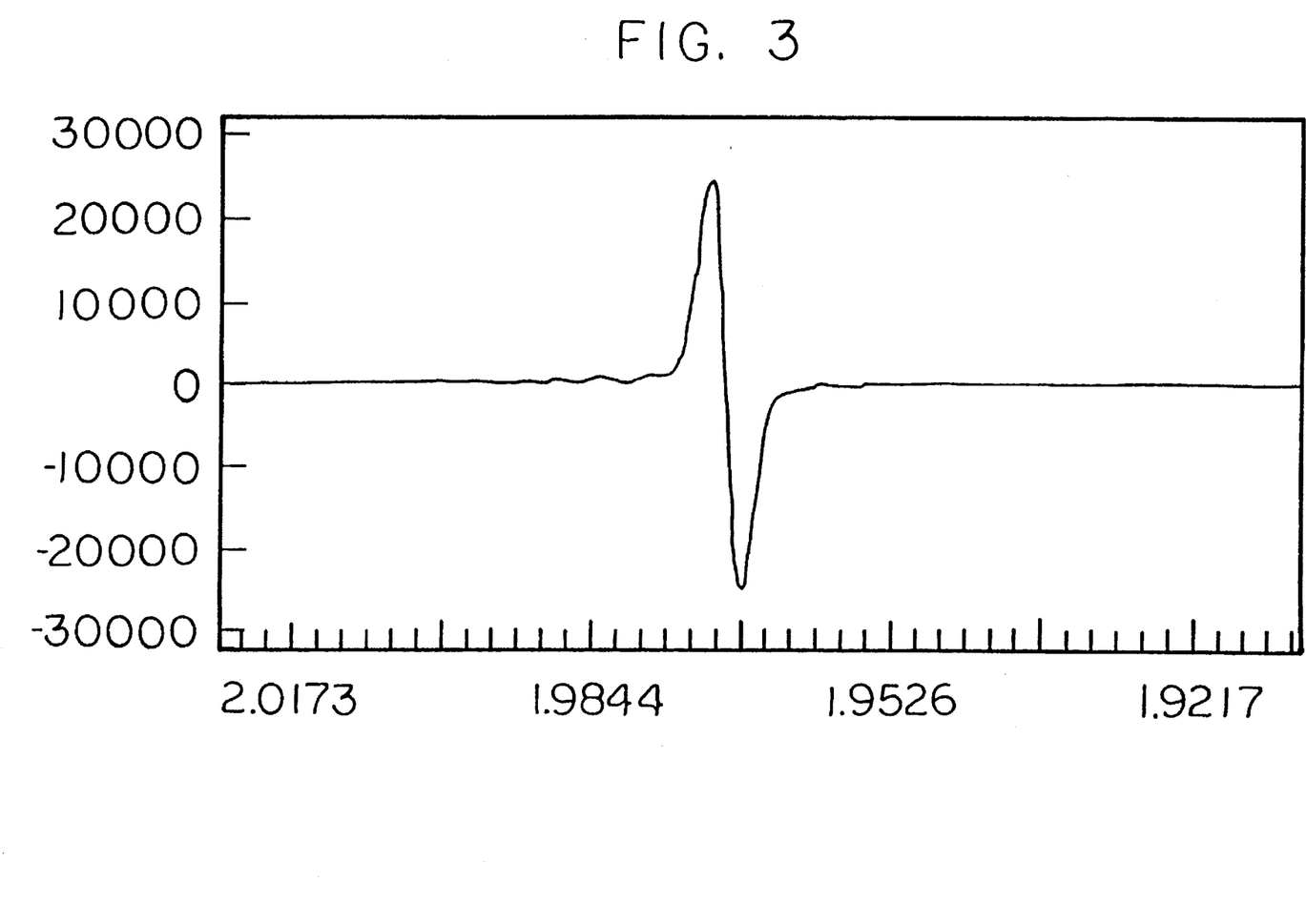
FIG. 3 is an electron spin resonance spectrogram of the product obtained in Example 60.

According to the present invention in its most generic description, there is provided an addition polymerization catalyst comprising:

(i) a metal complex corresponding to the formula: $Cp_a(ZY)_bML_c$, wherein:

a is 1 or 2;

b is 0 or 1;

c is 1 or 2;

the sum of a, b and c is 3;

Cp independently each occurrence is a cyclopentadienyl group π-bound to M, or a hydrocarbyl, silyl, halo, halohydrocarbyl, hydrocarbylmetalloid or halohydrocarbylmetalloid substituted derivative of said cyclopentadienyl group, said Cp containing up to 50 nonhydrogen atoms, and, when a is 2, optionally both Cp groups may be joined together by a bridging group;

L independently each occurrence is hydride, halo, or a monovalent anionic ligand selected from covalently bonded hydrocarbyl, silyl, amido, phosphido, alkoxy, aryloxy, and sulfido groups optionally being further substituted with amine, phosphine, ether, and thioether; mixtures thereof; said ligand having up to 50 nonhydrogen atoms, with the proviso that in at least one occurrence L is a stabilizing ligand comprising an amine, phosphine, ether or thioether functionality able to form a coordinate-covalent bond or chelating bond with M, or except when a is 2, comprising an ethylenic unsaturation able to form an η3 bond with M;

M is a metal of Group 4 of the Periodic Table of the Elements in the +3 oxidation state;

Y is a linking group comprising nitrogen, phosphorus, oxygen or sulfur covalently bonded to M and Z through said nitrogen, phosphorus, oxygen or sulfur atom;

Z is a divalent moiety comprising oxygen, nitrogen, phosphorous, boron, or a member of Group 14 of the Periodic Table of the Elements, said moiety having up to 30 nonhydrogen atoms;

the ligand moiety consisting of -Cp-Z-Y- being dianionic and having the ionic charges residing formally on Cp and Y;

and, when b is 0 and optionally when b is 1, (ii) an activating cocatalyst.

In accordance with one embodiment of the above generic description of the invention there is provided an addition polymerization catalyst comprising in combination:

(i) a metal complex, A$_1$, corresponding to the formula:

$$Cp'_2ML', \tag{Ia}$$

wherein:

Cp' independently each occurrence is a cyclopentadienyl group π-bound to M, or a hydrocarbyl, silyl, halo, halohydrocarbyl, hydrocarbylmetalloid or halohydrocarbylmetalloid substituted derivative of said cyclopentadienyl group, said Cp' containing up to 50 nonhydrogen atoms, and optionally both Cp groups may be joined together by a bridging group;

M is a metal of Group 4 of the Periodic Table of the Elements in the $^+$3 oxidation state;

L' is a monovalent anionic stabilizing ligand selected from the group consisting of: covalently bonded hydrocarbyl, silyl, amido, phosphido, alkoxy, aryloxy, sulfido groups and mixtures thereof, said group being further substituted with an amine, phosphine, ether, or thioether containing substituent able to form a coordinate-covalent bond or chelating bond with M; said ligand having up to 50 nonhydrogen atoms; and (ii) an activating cocatalyst.

Preferably in accordance with the present invention the ratio of metal complex to activating cocatalyst is from 1:0.01 to $1:10^6$.

In a further embodiment there is provided an addition polymerization catalyst comprising in combination:

(i) a metal complex, $A_2$, corresponding to the formula $$Cp''ML''_2, \qquad (Ib)$$

wherein:

Cp" is a cyclopentadienyl group π-bonded to M, or a hydrocarbyl, silyl, halo, halohydrocarbyl, hydrocarbylmetalloid, or halohydrocarbylmetalloid substituted derivative thereof, said Cp" containing up to 50 nonhydrogen atoms;

M is a metal of Group 4 of the Periodic Table of the Elements in the $^+3$ oxidation state;

L" independently each occurrence is hydride, halo, or a monovalent anionic ligand selected from the group consisting of covalently bonded hydrocarbyl, silyl, amido, phosphido, alkoxy, aryloxy, and sulfido groups; mixtures thereof; and amine, phosphine, ether, and thioether derivatives of the foregoing, said ligand having up to 50 nonhydrogen atoms, with the proviso that in at least one occurrence L" is a stabilizing ligand comprising an amine, phosphine, ether or thioether functionality able to form a coordinate-covalent bond or chelating bond with M, or comprising an ethylenic unsaturation able to form an η3 bond with M; and (ii) an activating cocatalyst.

Preferably the activating cocatalyst is present in an amount to provide a ratio of metal complex to activating cocatalyst from 1:0.01 to $1:10^6$.

In a still further embodiment of the present invention there is provided a metal complex, $A_3$, corresponding to the formula:

(Ic)

wherein:

M is a metal of Group 4 of the Periodic Table of the Elements in the $^+3$ oxidation state;

Cp''' is a cyclopentadienyl group, or a hydrocarbyl, silyl, halo, halohydrocarbyl, or hydrocarbylmetalloid substituted derivative thereof, said Cp''' containing up to 50 nonhydrogen atoms;

Z is a divalent moiety comprising oxygen, nitrogen, phosphorous, boron, or a member of Group 14 of the Periodic Table of the Elements said moiety having up to 30 nonhydrogen atoms;

Y is a linking group comprising nitrogen, phosphorus, oxygen or sulfur covalently bonded to M and Z through said nitrogen, phosphorus, oxygen or sulfur atom, the ligand moiety consisting of -Cp'''-Z-Y- being dianionic and having the ionic charges residing formally on Cp''' and Y; and L''' is a monovalent stabilizing ligand selected from the group consisting of L' and $C_{3-15}$hydrocarbyl groups comprising an ethylenic unsaturation able to form an η3 bond with M.

The above complexes, $A_3$, are suitable for use in polymerization of addition polymerizable monomers alone or optionally in the presence of an activating cocatalyst. In the latter event there is provided an addition polymerization catalyst comprising:

(i) the complex, $A_3$, and (ii) an activating cocatalyst.

The activating cocatalyst is preferably used in an amount to provide a ratio of metal complex to activating cocatalyst from 1:0.01 to $1:10^6$.

It is believed, without agreeing to be bound by such belief, that the metal complexes $A_1$, $A_2$, and $A_3$ when combined with the activating cocatalyst are converted into cationic metal complexes wherein the metal is in the +3 oxidation state. Evidence for this belief is established by electron spin resonance spectroscopy (ESR) and by the fact that solutions of the metal complexes in combination with the activating cocatalyst, especially tris(perfluorophenyl)boron are conductive in cyclic voltammetry analysis without added supporting electrolyte, whereas the complex alone is not conductive under the same conditions.

The presence of the above identified stabilizing ligand in the complexes of the invention results in improved complex stability and greatly improved usefulness in the formation of catalysts. The catalysts formed from these complexes by combination with the activating cocatalyst additionally possess higher activity and are more efficient addition polymerization catalysts than catalysts formed from corresponding complexes lacking such stabilizing ligand group.

The metal complexes, $A_1$, may be prepared by a process comprising contacting a Group 4 metal complex corresponding to the formula:

$$Cp'_2M^*XL' \qquad (IIa)$$

wherein Cp' and L' are as previously defined, and

M* is a metal of Group 4 of the Periodic Table of the Elements in the $^+$4 oxidation state; and X is halide or $C_{1-10}$hydrocarbyloxide, with a reducing agent under reducing conditions to form the Group 4 metal complex.

The metal complexes, $A_2$, may be prepared by a process comprising contacting a Group 4 metal complex corresponding to the formula:

$$Cp''M^*XL''_2 \qquad (IIb)$$

wherein Cp" and L" are as previously defined, and

M* is a metal of Group 4 of the Periodic Table of the Elements in the $^+$4 oxidation state; and X is halide or $C_{1-10}$ hydrocarbyloxide, with a reducing agent under reducing conditions to form the Group 4 metal complex.

Finally, the metal complexes, $A_3$, may be prepared by a process comprising contacting a Group 4 metal complex corresponding to the formula:

IIc wherein Cp''', Z, Y, M*, X and L''' are as previously defined, with a reducing agent under reducing conditions to form the Group 4 metal complex.

There are also provided polymerization processes comprising contacting an addition polymerizable monomer or monomers with the foregoing catalysts under polymerization conditions and recovering the resulting polymer.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

By the term "stabilizing ligand" is meant that the ligand group stabilizes the metal complex through either:

1) a nitrogen, phosphorus, oxygen or sulfur chelating bond, or 2) an $\eta^3$ bond with a resonant, delocalized π-electronic structure.

Examples of stabilizing ligands of group 1) for use according to the present invention include alkyl, cycloalkyl, aryl, silyl, amido or phosphido ligands substituted with one or more aliphatic or aromatic ether-, thioether-, amine- or phosphine- functional groups, especially such amine or phosphine groups that are tertiary substituted, said stabilizing ligand having from 3 to 30 nonhydrogen atoms. Most preferred group 1) stabilizing ligands are 2-dialkylaminobenzyl or 2-(dialkylaminomethyl)phenyl groups containing from 1 to 4 carbons in the alkyl groups.

Examples of stabilizing ligands of group 2) for use according to the present invention, include linear $C_{3-15}$hydrocarbyl groups containing ethylenic unsaturation, such as allyl, 1-methylallyl, 2-methylallyl, 1,1-dimethylallyl, 1,2,3-trimethylallyl, 1-phenyl-3-benzylallyl or 1,1-diphenyl-3-(diphenylmethyl)allyl groups.

Preferred substituents of the groups Cp, Cp" and Cp''' are hydrocarbyl (including hydrocarbylene) and halosubstituted hydrocarbyl groups, said groups having from 1 to 30 carbons, and $C_{1-30}$ hydrocarbyl or halohydrocarbyl substituted metalloid radicals wherein the metalloid is an element from Group 14 of the Periodic Table of the Elements.

Exemplary hydrocarbyl radicals include straight and branched alkyl radicals, cyclic aliphatic hydrocarbon radicals, alkyl-substituted cyclic aliphatic hydrocarbon radicals, aromatic radicals and alkyl-substituted aromatic radicals. Preferred are methyl, ethyl, butyl and phenyl radicals. Exemplary organometalloid radicals include straight and branched chain silyl radicals, alkyl-substituted silyl radicals, germyl radicals and divalent derivatives of the foregoing. Preferred are trimethylsilyl, triethylsilyl, ethyldimethylsilyl, methyldiethylsilyl, dimethyl-t-butylsilyl, triphenylsilyl, triphenylgermyl, and trimethylgermyl radicals.

More particularly, suitable cyclopentadienyl or substituted cyclopentadienyl groups in complexes $A_1$ are illustrated by the formula:

wherein:

R' is hydrogen, or a group selected from silyl, hydrocarbyl, and combinations thereof having up to 30 carbon or silicon atoms, or two R' groups together form a divalent derivative of such group.

Preferably, R' independently each occurrence is hydrogen, methyl, ethyl, propyl, butyl, pentyl, hexyl, (including where appropriate all isomers), cyclopentyl, cyclohexyl, norbornyl, benzyl, or phenyl or two R' groups are linked together thereby forming an indenyl, tetrahydroindenyl, fluorenyl, tetrahydrofluorenyl, or octahydrofluorenyl group in place of the cyclopentadienyl group.

Exemplary metal complexes of formula $A_1$ are: biscyclopentadienyl 2-(N,N-dimethylamino)benzyl titanium, bis(methylcyclopentadienyl) 2-(N,N-dimethylamino)benzyl titanium, bis(t-butylcyclopentadienyl) 2-((N,N-dimethylamino)methyl)phenyl titanium, bis(pentamethylcyclopentadienyl) 2-(N,N-dimethylamino)benzyl titanium, bis(indenyl)(2-N,N-dimethylamino)benzyl titanium, bis(fluorenyl) (2-N,N-dimethylamino)benzyl titanium, and corresponding zirconium and hafnium derivatives.

Additional bis-cyclopentadienyl compounds of formula $A_1$ include those containing a bridging group linking the cyclopentadienyl groups. Preferred bridging groups are those corresponding to the formula $(ER''_2)_x$ wherein E is silicon or carbon, R", independently each occurrence is hydrogen or a group selected from silyl, hydrocarbyl and combinations thereof, said R" having up to 30 carbon or silicon atoms, and x is 1 to 8. Preferably R" independently each occurrence is methyl, benzyl, tert-butyl, or phenyl.

Examples of the foregoing bridged cyclopentadienyl group containing complexes are compounds corresponding to the formula:

wherein:

M, L', E, R' R" and x are as previously defined.

Such bridged structures are especially suited for the preparation of polymers having stereoregular molecular structure. In such capacity it is preferred that the complex be nonsymmetrical or possess a chiral, stereorigid structure. Examples of the first type are compounds possessing different delocalized π-bonded systems, such as one cyclopentadienyl group and one indenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem,* 232, 233–47, (1982).

Exemplary bridged cyclopentadienyl complexes of formula Ia are: (dimethylsilyl-bis-cyclopentadienyl) titanium 2-(N,N-dimethylamino)benzyl, (dimethylsilyl-bis-cyclopentadienyl) titanium 2-((N,N-dimethylamino)methyl)phenyl, (dimethylsiyl-bis-t-butylcyclopentadienyl) titanium 2-(N,N-dimethylamino)benzyl, (dimethylsilyl-bis-tetramethylcyclopentadienyl) titanium 2-(N,N-dimethylamino)benzyl, (dimethylsilyl-bis-indenyl) titanium 2-(N,N-dimethylamino)benzyl, (isopropylidene-cyclopentadienyl)-fluorenyl) titanium 2-(N,N-dimethylamino)benzyl, [2,2'-biphenyldiylbis(3,4-dimethyl-1-cyclopentadienyl)]titanium 2-(N,N-dimethylamino)benzyl, [6,6-dimethyl-2,2'biphenyl-bis(3,4-dimethyl-1-cyclopentadienyl)] titanium 2-(N,N-dimethylamino)benzyl, and corresponding zirconium and hafnium complexes.

Exemplary complexes of formula $A_2$ include cyclopentadienyl titanium allyl chloride, t-butylcyclopentadienyl titanium allyl chloride, pentamethylcyclopentadienyl titanium allyl chloride, pentamethylcyclopentadienyl titanium allyl methoxide, n-butylcyclopentadienyl titanium allyl isopropoxide, pentamethylcyclopentadienyl titanium allyl phenoxide, cyclopentadienyl titanium (2-methylallyl) chloride, ethylcyclopentadienyl titanium (2-methylallyl) ethoxide, cyclopentadienyl titanium 2-(N,N-dimethylamino)benzyl chloride, pentamethylcyclopentadienyl titanium 2-(N,N-dimethylamino)benzyl bromide, cyclopentadienyl titanium 2-(N,N-dimethylamino)benzyl methoxide, n-butylcyclopentadienyl titanium 2-((N,N-dimethylamino)methyl)phenyl isopropoxide, cyclopentadienyl titanium allyl dimethylamide, n-butylcyclopentadienyl titanium allyl dimethylamide, t-butylcyclopentadienyl titanium allyl diethylamide, cyclopentadienyl titanium diallyl, cyclopentadienyl titanium 2-(methylallyl) dimethylamide, cyclopentadienyl titanium (2-methylallyl) (di-t-butylamide), cyclopentadienyl titanium 2-(N,N-dimethylamino)benzyl dimethylamide, pentamethylcyclopentadienyl titanium 2-(N,N-dimethylamino)benzyl dimethylamide, methylcyclopentadienyl titanium methyl 2-(N,N-dimethylaminobenzyl), methylcyclopentadienyl titanium benzyl 2-(N,N-dimethylamino)benzyl, methylcyclopentadienyl titanium trimethylsilylmethyl 2-(N,N-dimethylamino)benzyl, pentamethylcyclopentadienyl titanium methyl 2-(N,N-dimethylaminobenzyl), pentamethylcyclopentadienyl titanium trimethylsilylmethyl 2-(N,N-dimethylamino)benzyl, and corresponding zirconium and hafnium complexes.

Illustrative cyclic complexes, $A_3$, that may be employed in the practice of the present invention include: (tert-butylamido)dimethyl(tetramethyl-$\eta^5$-cyclopentadienyl)silane 2-(N,N-dimethylamino)benzyl titanium, (phenylamido)dimethyl(tetramethyl-$\eta^5$-cyclopentadienyl)silane 2-(N,N-dimethylamino)benzyl titanium, (tert-butylamido)(tetramethyl-$\eta^5$-cyclopentadienyl)-1,2-ethanediyl allyl titanium, (tert-butylamido)(tetramethyl-$\eta^5$-cyclopentadienyl)-1,2-ethanediyl 2-(dimethylamino)benzyltitanium, (methylamido)(tetramethyl-$\eta^5$-cyclopentadienyl)-1,2-ethanediyl allyl titanium, (tert-butylamido)dibenzyl(tetramethyl-$\eta^5$-cyclopentadienyl)silane 2-(N,N-dimethylamino)benzyl titanium, (benzylamido)dimethyl($\eta^5$-cyclopentadienyl)silane 2-((N,N-dimethylamino)methyl)phenyl titanium, (phenylphosphido)dimethyl(tetramethyl-$\eta^5$-cyclopentadienyl)silane 2-(dimethylamino)benzyl titanium, (tert-butylamido)-dimethyl(tetramethyl-$\eta^5$-cyclopentadienyl)silane allyl titanium, (methylamido)cyclotetramethylene($\eta^5$-octahydrofluorenyl)silane 2-(N,N-dimethylamino)benzyl titanium, (methylamido)cyclotetramethylene($\eta^5$-octahydrofluorenyl)silane 2-(N,N-dimethylamino)benzyl titanium, and corresponding zirconium or hafnium complexes.

Preferred cyclic complexes, $A_3$, are amidosilane- or amidoalkanediyl-compounds corresponding to the formula:

(V)

wherein:
M, L''', E, R', and R'' are as previously defined;
Y' is nitrogen;
R''' is a group selected from silyl, hydrocarbyl and combinations thereof, said group or combination having up to 30 carbon or silicon atoms; and
m is 1 or 2.

Preferably R''' is methyl, ethyl, propyl, butyl, pentyl, hexyl, (including where appropriate all isomers), cyclopentyl, cyclohexyl, norbornyl, benzyl, or phenyl.

In the most preferred embodiment -(ER''$_2$)$_m$Y'R'''- is an amidosilane or amidoalkane group of up to 30 nonhydrogen atoms, especially, (tert-butylamido)(dimethylsilyl), (methylamido)(dimethylsilyl), or (tert-butylamido)-1-ethane-2-yl.

Highly preferably in complexes $A_1$, M is titanium and L' is 2-dimethylaminobenzyl. Highly preferably in complexes $A_2$, M is titanium and L'' is 2-dimethylaminobenzyl or allyl. Highly preferably in complexes $A_3$, M is titanium and L''' is 2-dimethylaminobenzyl or allyl.

By the term "reducing agent" herein is meant a metal or compound which, under reducing conditions causes M to be reduced from the +4 oxidation state to the +3 oxidation state. Examples of suitable metal reducing agents are alkali metals, alkaline earth metals, lead and zinc, alloys of alkali metals or alkaline earth metals such as sodium/mercury amalgam and sodium/potassium alloy. Examples of suitable reducing agent compounds are sodium naphthalenide, potassium graphite, and Grignard reagents. Most preferred reducing agents are the alkali metals or alkaline earth metals, especially magnesium.

By the term "reducing conditions" is meant the use of diluents and temperatures that allow the desired reduction to take place. Preferred temperatures are from 0° C. to 200° C., more preferably from 5° C. to 120° C. and most preferably from 10° C. to 50° C. Preferred diluents are polar solvents, more preferably $C_{1-6}$ aliphatic ethers, most preferably tetrahydrofuran, 1,2-dimethoxyethane or diethyl ether.

The term "activating cocatalyst" as used herein refers to a secondary component that renders the metal complex catalytically effective or improves the catalytic effectiveness of the metal complex as an addition polymerization catalyst. Examples of the activating cocatalysts for use herein include aluminum compounds containing an Al—O bond such as the alkylalumoxanes, especially methylalumoxane and isobutyl modified methylalumoxane; aluminum alkyls; aluminum halides; alkylaluminum halides; Lewis acids other than any of the foregoing list; and mixtures of the foregoing.

Preferred Lewis acids are those compounds corresponding to the formula: R''''$_3$B, wherein R'''' independently each occurrence is selected from hydrogen, silyl, hydrocarbyl, halohydrocarbyl, alkoxide, aryloxide, amide or combinations thereof, said R'''' having up to 30 nonhydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Preferred activating cocatalysts include trimethylaluminum, triisobutylaluminum, methylalumoxane, ethylalumoxane, chlorodiethylaluminum, dichloroethylaluminum, triethylboron, trimethylboron, triphenylboron and halogenated, especially fluorinated, triphenyl boron compounds.

Most highly preferred activating cocatalysts include triethylaluminum, methylalumoxane, and fluoro-substituted triaryl borons such as tris(4-fluorophenyl)boron, tris(2,4-difluorophenylboron), tris(3,5-bis(trifluoromethyl)phenyl)boron, tris(pentafluorophenyl)boron, pentafluorophenyldiphenylboron, and bis(pentafluorophenyl)phenylboron. Such fluoro-substituted triarylboranes may be readily synthesized according to techniques such as those disclosed in Marks, et al. *J. Am. Chem. Soc.*, 113, 3623–3625 (1991).

A neutral Lewis base may additionally be present in combination with the complexes and catalysts of the invention. Suitable neutral Lewis bases include, for example, organic compounds containing oxygen, nitrogen, phosphorus or sulfur, or olefins. More specifically, examples of suitable electron donating compounds include organic amines, amides, ketones, nitriles, phosphines, phosphorylamides, esters, ethers (including cyclic ethers such as furans), thioethers and thioesters. Preferred are such compounds containing up to 20 nonhydrogen atoms. A highly preferred electron donating agent is tetrahydrofuran (THF).

It has been previously reported that Lewis bases such as THF have a severe degrading effect on the catalytic activity of cyclopentadienyl complexes of Group 4 metals in the +4 oxidation state. Jordan, et al,. *J. Am. Chem. Soc.*, 108, 7410–7411 (1986) at 7410, reported that "Addition of THF or other donor ligands slows the polymerization rate dramatically and in THF or $CH_3CN$ solvents no activity is observed". Similarly, Bochmann et al., *Polyhedron*, 8 (13–14), 1838–1843 (1989) reported that bis(pentamethylcyclopentadienyl)titanium(IV) methyl tetraphenylborate prepared in THF solvent was inactive for ethylene polymerization. Surprisingly, the presence of a neutral Lewis base does not necessarily adversely affect the catalytic activity of the metal complexes of the present invention, particularly the complexes of formula $A_3$.

The catalyst can be formed by combining the activating cocatalyst (where required) with the complex, with or without a neutral Lewis base, optionally in the presence of a diluent. Complexes that need no activating cocatalyst may be used to polymerize addition polymerizable monomers without further additives or in combination with the above neutral Lewis base and optionally in the presence of a diluent. The preparation may be conducted in the presence of one or more addition polymerizable monomers, if desired. Preferably, the catalysts are prepared at a temperature within the range from $-100°$ C. to $300°$ C., preferably $0°$ C. to $250°$ C., and most preferably $0°$ C. to $100°$ C. Suitable solvents include straight and branched-chain hydrocarbons such as isobutane, butane, pentane, hexane, heptane, octane, and mixtures thereof; cyclic and alicyclic hydrocarbons such as cyclohexane, cycloheptane, methytcyclohexane, methylcycloheptane; perfluorinated hydrocarbons such as perfluorinated $C_{4-10}$ alkanes; and aromatic and alkyl-substituted aromatic compounds such as benzene, toluene and xylene. Suitable solvents also include liquid olefins which may act as monomers or comonomers including ethylene, propylene, butadiene, cyclopentene, 1-hexene, 3-methyl-1-pentene, 4-methyl- 1-pentene, 1,4-hexadiene, 1-octene, 1-decene, styrene, divinylbenzene, 4-vinylcyclohexene, allylbenzene and vinyltoluene (including all isomers alone or in admixture). Preferred solvents are aliphatic hydrocarbons especially $C_5-C_{10}$ alkanes or cycloalkanes and mixtures thereof. Such a mixture is available commercially under the trade designation Isopar™ E, available from Exxon Chemicals. If no cocatalyst is necessary, the complex itself is contacted with the addition polymerizable monomer.

"Addition polymerizable monomers" usefully polymerized according to the present invention include, for example, ethylenically unsaturated monomers, cyclic olefins, acetylenic compounds, conjugated or nonconjugated dienes and polyenes. Specific examples include $C_{2-20}$ olefins, styrene, halo- or hydrocarbyl substituted styrenes, divinylbenzene, 4-vinylcyclohexene, tetrafluoroethylene, vinylbenzocyclobutane, butadiene, isoprene, 1,4-hexadiene, cyclobutene, cyclopentene, cyclohexene, norbornene, ethylidene norbornene, acetylene, and mixtures thereof. Preferred monomers include the $C_{2-10}$ α-olefins especially ethylene, propylene, isobutylene, 1-butene, 1-hexene, 4-methyl-1-pentene, styrene, and 1-octene.

In general, the polymerization may be accomplished at conditions well known in the prior art for Ziegler-Natta or Kaminsky-Sinn type polymerization reactions, that is, temperatures from $0°$ to $250°$ C. and pressures from atmospheric to 1000 atmospheres (100 MPa). Suspension, solution, slurry, gas phase or other process condition may be employed if desired. The catalyst may be supported and such supported catalyst may be employed in the polymerizations of this invention. Preferred supports include alumina and silica.

The equivalent ratio of metal complex to activating cocatalyst (where employed) is preferably in a range from 1:0.5 to $1:10^4$, more preferably from 1:0.75 to $1:10^3$, most preferably 1:1 to 1:10. In most polymerization reactions the equivalent ratio of catalyst:polymerizable compound employed is from $10^{-12}:1$ to $10^{-1}:1$, more preferably from $10^{-9}:1$ to $10^{-4}:1$.

Having described the invention the following examples are provided as further illustration thereof and are not to be construed as limiting. Unless stated to the contrary all parts and percentages are expressed on a weight basis.

EXAMPLES 1–58 i) Preparation of Reduced Metal
Complex—(Tert-butylamido)dimethyl(tetramethyl-$\eta^5$-cyclopentadienyl)silane
(2-N,N-dimethylamino)benzyl titanium,
$(CH_3)_4C_5Si(CH_3)_2N—C(CH_3)_3)Ti$
$(o-CH_2C_6H_4N(CH_3)_2)$ In a drybox, 1.65 g (4.45 mmol) of $TiCl_3(THF)_3$ and 2.29 g (4.46 mmol) of $(MgCl)_2((CH_3)_4C_5Si(CH_3)_2N—C(CH_3)_3)(THF)_2$ were mixed together in a 100 ml flask. Tetrahydrofuran (THF) (50 mL) was added to give a purple solution. After 15 minutes, 0.63 g (4.46 mmol) of o-$LiCH_2C_6H_4N(CH_3)_2$ was added. After 30 minutes, the volatile materials were removed under reduced pressure to yield a red-brown solid. Pentane (50 mL) was added, the solution was filtered, and the volume reduced to 40 mL. This concentrated solution was cooled to $-30°$ C. Red crystals were isolated by filtration and dried under reduced pressure.

The electron paramagnetic resonance (EPR) spectrum of this material exhibited a single line at room temperature (g=1.974) and 2 lines at $77°$ K. The X-ray crystal structure had final cell parameters corresponding to a triclinic unit cell. Cell parameters were$_c$: a=9.922(4), b=14.366(9), c=9.857(5) (angstroms); α=104.35(6), β=111.69(4 ), γ=99.61(6); V=1212(1) (angstroms$^3$).

ii) Alternate Preparation of
(Tert-butylamido)dimethyl(tetramethyl-$\eta^5$-cyclopentadienyl)silane 2-(dimethylamino)benzyl titanium—Reduction of Ti(IV) Complex $TiCl_3(THF)_3$ suspended in THF was contacted with equal molar quantities of solid tetramethylcyclopentadienyldimethyl-t-butylaminosilane-diGrignard—THF complex $((CH_3)_4C_5Si(CH_3)_2$-N-t-Bu $Mg_2Cl_2(THF)_2)$. To the resulting Ti(III) complex was added a sufficient amount of a 1.56M solution of methylene chloride in THF to provide a 0.5:1 molar ratio of methylene chloride to the metal complex. After one hour the product, $(CH_3)_4C_5Si(CH_3)_2N$-t-BuTlCl$_2$, was recovered by extraction in pentane. In an argon filled glovebox, 0.990 g (2.69 mmol) of the (tert-butylamido)dimethyl(tetramethyl-$\eta^5$-cyclopentadienyl)silane titanium dichloride and 0.389 g (2.76 mmol) of Li(o-CH$_2$(C$_6$H$_4$ )N(CH$_3$)$_2$) were mixed together in a 100 mL flask. Pentane (75 mL) was added and the mixture stirred for 16 hours to provide an orange colored product. The mixture was filtered through a sintered glass frit. The solids were washed with pentane and the filtrates combined. Pentane solvent was removed under reduced pressure leaving a solid residue which was washed with cold pentane. The pentane wash was decanted from the residue and the product dried under reduced pressure giving 0.96 g. of an orange solid. $^1$H NMR analysis confirmed the product's identity as (tert-butylamido)dimethyl(tetramethyl-$\eta^5$ -cyclopentadienyl)silane titanium 2-(N,N-dimethylamino)benzyl chloride. Yield was 76 percent.

The solid product (0.490 g, 1.05 mmole) obtained above was added to 50 ml of tetrahydrofuran. Magnesium powder (30 mg) was then added. The mixture was stirred at 25° C. After 30 minutes the orange color of the solution changed to brown. After 4 hours the solvent was removed under reduced pressure. The solid residue was extracted with pentane (3×25 ml). The pentane extracts were filtered through a sintered glass frit, combined, and the pentane removed under reduced pressure to give 0.452 g (quantitative yield) of rose-purple microcrystalline solid, identified as (tert-butylamido)dimethyl(tetramethyl-$\eta^5$-cyclopentadienyl)silane 2-(N,N-dimethylamino)benzyl titanium by comparison of its cyclic voltamagram with that of the material obtained in Preparation i.

iii) Preparation of Reduced Metal Complex—(Tert-butylamido)dimethyl(tetramethyl-$\eta^5$-cyclopentadienyl)silane allyl titanium (III), (($CH_3$)$_4$C$_5$Si(CH$_3$)$_2$NC(CH$_3$)$_3$)Ti(C$_3$H$_5$)

In a drybox, 0.30 g of TiCl$_3$(THF)$_3$ and 0.42 g of (MgCl)$_2$((CH$_3$)$_4$C$_5$Si(CH$_3$ )$_2$N—C(CH$_3$)$_3$)(THF)$_2$ were mixed in a Schlenk tube. 20 mL of THF was added to give a purple solution. The Schlenk tube was sealed and removed to a Schlenk line, and the solution was cooled to −30° C. 0.81 mL of 1.0M allylmagnesium bromide was added by syringe. After 20 minutes, the solution was warmed to 0° C. and the volatile materials were removed under reduced pressure to yield a dark solid. While keeping the flask at 0° C. pentane (30 mL) was added, and the deep red solution was filtered, concentrated to 5–7 mL, and cooled to −40° C. Red crystals were isolated by filtration and dried in 22 percent yield. The EPR spectrum of this material exhibited a single line at room temperature and 2 lines at 77° K.

iv) Preparation of Reduced Metal Complex—Biscyclopentadienyl 2-(N,N-dimethylamino)benzyl titanium (III), Cp$_2$Ti(o-CH$_2$C$_6$H$_4$N(CH$_3$)$_2$)

This metal complex was prepared according to the procedure of *J. Am. Chem. Soc.* 100, 8068–8073 (1978) by reaction of stoichiometric amounts of biscyclopentadienyltitanium (III) chloride and 2-dimethylaminobenzyl lithium in diethylether.

v) Preparation of Reduced Metal Complex—(Tert-butylamido)dimethyl(tetramethyl-$\eta^5$-cyclopentadienyl)silane 1,2,3-trimethylallyl titanium (III)

In a glovebox under an inert atmosphere, (tert-butylamido)dimethyl(tetramethyl-$\eta^5$-cyclopentadienyl)silanetitanium (IV) dichloride (0.500 g, 0.0014 mol) was dissolved in 30 mL of diethyl ether giving a yellow solution. To this solution was added 3-methyl-1,3-pentadiene (0.31 ml, 0.0027 mol) and i-PrMgCl (1.18 ml, 0.0028 mol). Gas evolution was noted and the color became red/purple. After 50 minutes the solvent was removed and the product dried. Extraction with pentane (5×10 ml) and drying under reduced pressure gave the desired product as a red solid.

POLYMERIZATION

Several catalyst compositions were prepared by combining the metal complex and a cocatalyst in a stirred polymerization reactor. The cocatalysts used were tris(perfluorophenyl)borane (I), methylalumoxane (1M in toluene, available from Schering (AG) (II), trimethyl aluminum (III), triisobutylaluminum (IV), isobutyl modified methylalumoxane (1M in toluene, MMAO, type 3A, available from Texas Alkyls Corp.) (V), triethylaluminum (VI), phenyl bis(perfluorophenyl) borane (VII), and triphenyl borane (VIII). Accordingly, a 2 L stirred reactor was charged with the desired amounts of mixed alkane solvent (isopar-E™ available from Exxon Chemicals Inc.) and 1-octene comonomer. The reactor was heated to the polymerization temperature, hydrogen was added by differential pressure expansion from a ~75 mL addition tank, and the reactor was saturated with ethylene to the desired pressure. Metal complex and cocatalyst (where used) were mixed in a drybox by syringing the desired amount of 0.0050M metal complex solution (in Isopar-E™ or toluene) into a solution of the cocatalyst (in Isopar-E™ or toluene). This solution was then transferred to a catalyst addition tank and injected into the reactor. The same procedure was employed when no cocatalyst was employed excepting only the complex was added to the reactor. The polymerization was allowed to proceed for the desired time and the solution was removed from the reactor and quenched with isopropanol. A hindered phenol antioxidant (Irganox™ 1010, available from Ciba Geigy Corp.) was added and the polymers (linear low density polyethylenes) were air-dried for 16 hours and then dried in a reduced pressure oven. Results are contained in Table I.

TABLE I

| Ex. | Complex | Amt. (μmol) | Cocatalyst | Amt. (μmol) | Solvent (g) | 1-Octene (g) | Ethylene (MPa) | H$_2$ (ΔkPa) | Temp (°C.) | Time (min) | Polymer (g) | Efficiency (g poly/g Ti) |
|---|---|---|---|---|---|---|---|---|---|---|---|---|
| 1 | i | 5.00 | I | 5.0 | 715 | 143 | 3.1 | 69 | 130 | 10 | 112.6 | 470,146 |
| 2 | i | 5.00 | I | 5.0 | 715 | 143 | " | 69 | 130 | 10 | 83.2 | 347,390 |
| 3 | i | 2.50 | I | 2.5 | 715 | 143 | " | 34 | 120 | 18 | 62.3 | 520,251 |
| 4 | i | 10.00 | II | 2940 | 715 | 143 | " | 340 | 130 | 15 | 54.7 | 114,196 |
| 5 | i | 10.00 | II | 184 | 715 | 143 | " | 340 | 130 | " | 22.5 | 46,973 |
| 6 | i | 10.00 | II | 2940 | 715 | 143 | " | 340 | 130 | " | 58.5 | 122,129 |
| 7 | i | 10.00 | IV | 1000 | 715 | 143 | " | 340 | 130 | " | 23.7 | 49,478 |

TABLE I-continued

| Ex. | Complex | Amt. (μmol) | Cocatalyst | Amt. (μmol) | Solvent (g) | 1-Octene (g) | Ethylene (MPa) | $H_2$ (ΔkPa) | Temp (°C.) | Time (min) | Polymer (g) | Efficiency (g poly/g Ti) |
|---|---|---|---|---|---|---|---|---|---|---|---|---|
| 8 | i | 10.00 | II | 1470 | 787 | 72 | " | 34 | 160 | " | 17.8 | 37,161 |
| 9 | i | 10.00 | II | 2940 | 787 | 72 | " | 0 | 175 | " | 13.6 | 28,392 |
| 10 | i | 10.00 | II | 7350 | 715 | 143 | " | 340 | 130 | " | 53.7 | 112,109 |
| 11 | iii | 10.00 | II | 588 | 715 | 143 | " | 340 | 130 | " | 37.8 | 78,914 |
| 12 | iii | 10.00 | II | 441 | 715 | 143 | " | 340 | 130 | " | 23.1 | 48,225 |
| 13 | i | 0.50 | I | 1.5 | 740 | 118 | 3.4 | 170 | 100 | " | 62.2 | 2,597,077 |
| 14 | i | 1.50 | I | 3.0 | 788 | 70 | " | 90 | 160 | " | 20.0 | 285,317 |
| " | i | 1.00 | I | 3.0 | 740 | 118 | " | 340 | 140 | " | 30.7 | 640,919 |
| 16 | i | 1.00 | I | 3.0 | 740 | 118 | " | 0 | 140 | " | 18.7 | 390,397 |
| 17 | i | 0.75 | I | 1.5 | 691 | 167 | " | 90 | 120 | " | 45.5 | 1,266,527 |
| 18 | i | 0.75 | I | 1.5 | 788 | 70 | " | 260 | 120 | " | 44.8 | 1,247,042 |
| 19 | i | 0.75 | I | 3.0 | 691 | 167 | " | 90 | 120 | " | 43.2 | 1,202,505 |
| 20 | i | 1.00 | I | 3.0 | 740 | 118 | " | 170 | 140 | " | 17.2 | 359,081 |
| 21 | i | 1.50 | I | 6.0 | 788 | 70 | " | 260 | 160 | " | 12.4 | 172,582 |
| 22 | i | 0.75 | I | 1.5 | 788 | 70 | " | 90 | 120 | " | 41.6 | 1,157,968 |
| 23 | i | 1.00 | I | 3.0 | 740 | 118 | " | 170 | 140 | " | 10.1 | 210,856 |
| 24 | i | 0.75 | I | 3.0 | 788 | 70 | " | 90 | 120 | " | 45.2 | 1,258,177 |
| 25 | i | 1.00 | I | 3.0 | 740 | 118 | " | 170 | 140 | " | 16.3 | 340,292 |
| 26 | i | 1.00 | I | 3.0 | 740 | 118 | 3.4 | 170 | 140 | 15 | 12.6 | 263,048 |
| 27 | i | 10.00 | I | 30.0 | 740 | 118 | " | " | 180 | " | 12.5 | 26,096 |
| 28 | i | 1.00 | I | 3.0 | 837 | 21 | " | " | 140 | " | 43.0 | 897,704 |
| 29 | i | 1.00 | I | 3.0 | 740 | 118 | " | " | 140 | " | 27.9 | 582,463 |
| 30 | i | 0.75 | I | 3.0 | 691 | 167 | " | 260 | 120 | " | 39.4 | 1,096,729 |
| 31 | i | 1.00 | I | 3.0 | 740 | 118 | " | 170 | 140 | " | 20.2 | 421,712 |
| 32 | i | 1.50 | I | 6.0 | 691 | 167 | " | 91 | 160 | " | 5.1 | 70,981 |
| 33 | i | 1.50 | I | 3.0 | 691 | 167 | " | 91 | 160 | " | 5.8 | 80,724 |
| 34 | i | 1.00 | I | 3.0 | 644 | 215 | " | 170 | 140 | " | 13.8 | 288,100 |
| 35 | i | 1.50 | I | 3.0 | 691 | 167 | " | 260 | 160 | " | 8.4 | 116,910 |
| 36 | i | 1.00 | I | 5.0 | 740 | 118 | " | 170 | 140 | " | 17.0 | 354,906 |
| 37 | i | 1.50 | I | 6.0 | 691 | 167 | " | 260 | 160 | " | 6.9 | 96,033 |
| 38 | i | 0.75 | I | 1.5 | 691 | 167 | " | 260 | 120 | " | 50.9 | 1,416,841 |
| 39 | i | 1.50 | I | 3.0 | 788 | 70 | " | 260 | 160 | " | 7.3 | 101,601 |
| 40 | i | 0.75 | I | 3.0 | 788 | 70 | " | 260 | 120 | " | 29.7 | 826,722 |
| 41 | i | 1.00 | I | 1.0 | 740 | 118 | " | 170 | 140 | " | 7.8 | 162,839 |
| 42 | i | 1.50 | I | 6.0 | 788 | 70 | " | 90 | 160 | " | 2.9 | 40,362 |
| 43 | i | 1.00 | I | 3.0 | 740 | 118 | " | 170 | 140 | " | 13.3 | 277,662 |
| 44 | i | 2.50 | III | 2.5 | 740 | 118 | " | " | 120 | " | 1.6 | 13,361 |
| 45 | i | 2.50 | III | 5.0 | 740 | 118 | " | " | 120 | " | .7 | 5,846 |
| 46 | i | 2.50 | III | 7.5 | 740 | 118 | " | " | 120 | " | 0.7 | 5,846 |
| 47 | i | 2.50 | IV | 7.5 | 740 | 118 | " | " | 120 | " | 0.5 | 4,175 |
| 48 | i | 2.50 | V | 37.5 | 740 | 118 | " | " | 120 | " | 3.3 | 20,577 |
| 49 | i | 2.50 | VI | 3.7 | 740 | 118 | " | " | 120 | " | 8.2 | 68,476 |
| 50 | i | 2.50 | VI | 7.5 | 740 | 118 | " | " | 120 | " | 8.9 | 74,322 |
| 51 | i | 2.50 | VI | 25.0 | 740 | 118 | 3.4 | 170 | 120 | 15 | 9.1 | 75,992 |
| 52 | i | 2.50 | VI | 75.0 | 740 | 118 | " | " | " | " | 5.7 | 47,599 |
| 53 | iv | 2.50 | I | 7.5 | 740 | 118 | " | " | " | " | 36.3 | 303,132 |
| 54 | ii | 2.00 | I | 2.0 | 740 | 118 | " | " | 140 | " | 112.4 | 1,174,000 |
| 55 | ii | " | VII | 3.0 | " | " | " | " | 140 | " | 122.4 | 1,277,000 |
| 56 | ii | " | VIII | 3.0 | " | " | " | " | 140 | " | 119.5 | 1,247,000 |
| 57 | ii | " | — | 0.0 | " | " | " | " | " | " | 72.3 | 755,000 |
| 58 | v | 0.75 | I | 0.75 | 708 | 150 | " | " | 120 | " | 68.8 | 1,915,000 |

EXAMPLE 59

(i) Preparation of (Phenylamido)dimethyl(tetramethyl-η⁵-cyclopentadienyl)silane 2-(N,N-dimethylamino)benzyl titanium chloride In an argon filled glove box, 0.55 g (1.29 mmol) of (phenylamido)dimethyl(tetramethyl-η⁵-cyclopentadienyl)silane titanium dichloride (prepared according to Example 89 of EP-A-0416845 and 0.18 g (1.3 mmol) of 2-(N,N-dimethylamino)benzyl lithium were slurried in ~75 mL of pentane. The mixture turned from yellow to red after ~16 hours. The mixture was filtered and the solids were extracted with diethyl ether. The pentane and ether fractions were devolatilized under reduced pressure. $^1$H NMR analysis confirmed the product's identity from both fractions as (phenylamido)dimethyl(tetramethyl-η⁵-cyclopentadienyl)silane titanium 2-(N,N-dimethylamino)benzyl chloride. Total yield was 0.33 g, 53 percent.

(ii) Preparation of (Phenylamido)dimethyl(tetramethyl-η⁵-cyclopentadienyl)silane-2-(N,N-dimethylamino)benzyl titanium In an argon filled glove box 16 mg of magnesium powder was added to 0.33 g (0.68 mmol) of (phenylamido)dimethyl(tetramethyl-η⁵-cyclopentadienyl)silane 2-(dimethylamino)benzyl titanium chloride in ~40 mL of tetrahydrofuran (THF). After stirring for 6 hours the THF was removed under reduced pressure. The solid residue was extracted with pentane. The pentane extracts were filtered and combined and the pentane solvent removed under reduced pressure to give 0.29 g (94 percent yield) of (phenylamido)dimethyl(tetramethyl-η⁵ -cyclopentadienyl)silane-2-(N,N-dimethylamino)benzyl titanium, characterized by cyclic voltametry.

EXAMPLE 60

A 100 ml round bottom flask was loaded with 0.100 g of (tert-butylamido)dimethyl(tetramethyl-$\eta^5$-cyclopentadienyl)silane (2-N,N-dimethylamino)benzyl titanium. 30 ml of pentane were added to form a solution. To this solution was added, via pipet, 0.119 g of $B(C_6F_5)_3$ in 40 ml of pentane. Within minutes the solution become cloudy and a pink/orange solid precipitated from solution. The reaction mixture was stirred for an additional 15 minutes after which time the solid was collected by filtration and washed with fresh pentane (3×5 ml). Yield of the product (believed to be [(tert-butylamido)dimethyl(tetramethyl-$\eta^5$-cyclopentadienyl)silane titanium(III)]((2-N,N-dimethylamino)benzyl)trispentafluorophenylboron), after drying under reduced pressure was 0.205 g.

The ESR spectrum of this reaction product showed a single line at room temperature (g=1.97). The cycle voltamagram (in dimethyl ether (DME) with no supporting electrolyte) of the reaction product showed an irreversible reduction wave at −2.74 volts vs. ferrocene. Under similar conditions, the neutral complex, (tert-butylamido)dimethyl(tetramethyl-$\eta^5$-cyclopentadienyl)silane (2-N,N-dimethylamino)benzyl titanium, was not conductive and did not give a cyclic voltamagram. The fact that electrochemical measurements could be obtained in the absence of added supporting electrolyte strongly indicates that the activated complex was cationic.

Under the polymerization conditions of Example 54, the above activated complex used as a catalyst gave 28.8 g of ethylene/octene copolymer.

EXAMPLE 61

The reaction conditions of Example 59 were repeated to prepare the pink/orange cationic metal complex which was then redissolved in tetrahydrofuran thereby giving a purple solution. Addition of pentane caused precipitation of a purple solid which was collected by filtration, washed with fresh pentane, and dried.

The ESR spectrum of the purple product showed a single line at room temperature (g=1.97) and the cyclic voltamagram (in DME with no supporting electrolyte) showed an irreversible reduction wave at −2.74 volts vs. ferrocene. Under similar conditions, the neutral complex did not give a cyclic voltamagram thereby indicating that the purple solid was an ionic Ti+3 complex.

15 mg of the purple solid was combined with 0.5 mL of methanol and the resulting solution was analyzed by gc/mass spectroscopy. THF was identified in the solution, indicating that the purple solid contained the neutral Lewis base, THF. On this basis the purple solid was believed to be [(tert-butylamido)dimethyl(tetramethyl-$\eta^5$-cyclopentadienyl)silane titanium(III)(THF)]((2-N,N-dimethylamino)benzyl)trispentafluorophenylboron).

Under the polymerization conditions of Example 54, the above purple solid used as a catalyst gave 29.2 g of ethylene/octene copolymer.

EXAMPLE 62

(i) Preparation of
(t-Butylamido)dimethyl(tetramethyl-$\eta^5$-cyclopentadienyl)silane (1-phenyl-3-benzylallyl) titanium In an argon filled glove box, 0.50 g (1.4 mmol) of (t-butylamido)dimethyl(tetramethyl-$\eta^5$-cyclopentadienyl)silane titanium dichloride was dissolved into 30 mL of diethyl ether to give a yellow solution. 0.28 g (1.4 mmol) of 1,4-diphenyl-1,3 butadiene and 1.18 mL (2.8 mmole) of isopropyl magnesium chloride were added with stirring. Gas evolution occurred and the mixture darkened to a red/purple color over 50 minutes. The solvent was removed and the product was dried. The solid was extracted with pentane (5×10 mL) and dried under reduced pressure to give the product as a red/purple solid (0.545 g).

Under the polymerization conditions of Example 54, 68.7 g of ethylene/octene copolymer were produced. Catalyst efficiency was 717,000 g/g.

EXAMPLE 63

(i) Preparation of
(t-Butylamido)dimethyl(tetramethyl-$\eta^5$-cyclopentadienyl)silane
(1,1-diphenyl-3-(diphenylmethyl)allyl) titanium In an argon filled glove box, 0.50 g (1.4 mmol) of (t-butylamido)dimethyl(tetramethyl-$\eta^5$-cyclopentadienyl)silane titanium dichloride was dissolved into 30 mL of diethyl ether to give a yellow solution. 0.49 g (1.4 mmol) of 1,1,4,4-tetraphenyl-1,3-butadiene and 1.18 mL (2.8 mmole) of isopropyl magnesium chloride were added with stirring. Gas evolution occurred and the mixture darkened to a red color over 2 hours. The solvent was removed and the product was dried. The solid was extracted with pentane (4×15 mL) and dried under reduced pressure to give the product as a tacky, red solid.

Under the polymerization conditions of Example 54, 32.0 g of ethylene/octene copolymer were produced. Catalyst efficiency was 334,029 g/g.

We claim:

1. A metal complex corresponding to the formula:

wherein:

M is titanium in the +3 oxidation state;

Cp''' is a cyclopentadienyl group, or a hydrocarbyl, silyl, halo, halohydrocarbyl, or hydrocarbylmetalloid substituted derivative thereof, said Cp''' containing up to 50 nonhydrogen atoms;

Z is a divalent moiety comprising oxygen, nitrogen, phosphorous, boron, or a member of Group 14 of the Periodic Table of the Elements, said moiety having up to 30 nonhydrogen atoms;

Y is a linking group comprising nitrogen, phosphorus, oxygen or sulfur covalently bonded to M and Z through said nitrogen, phosphorus, oxygen or sulfur atom, the ligand moiety consisting of -Cp'''-Z-Y- being dianionic and having the ionic charges residing formally on Cp''' and Y; and

L''' is 2-di($C_1$–$C_4$ alkyl)aminobenzyl, 2-(di($C_1$–$C_4$ alkyl)aminomethyl)phenyl, allyl, 1-methylallyl, 2-methylallyl, 1,1-dimethylallyl, 1,2,3-trimethylallyl, 1-phenyl-3-benzylallyl or 1,1-diphenyl-3-(diphenylmethyl)allyl.

2. A complex according to claim 1 wherein Y is tertiary-butylamido.

3. A complex according to claim 1, wherein L''' is 2-(N,N-dimethylamino)benzyl.

4. A complex according to claim 1 selected from the group consisting of (tert-butylamido)dimethyl(tetramethyl-η5-cyclopentadienyl)silane 2-(N,N-dimethylamino)benzyl titanium (III), (tert-butyl-amido)dimethyl(tetramethyl-η5-cyclopentadienyl)silane allyl titanium (III), (tert-butyl-amido)dimethyl(tetramethyl-η5-cyclopentadienyl)silane 1,2,3-trimethylallyl titanium (III), (tert-butyl-amido)dimethyl(tetramethyl-η5-cyclopentadienyl)silane 1-phenyl-3-benzylallyl titanium (III), and (tert-butyl-amido)dimethyl(tetramethyl-η5-cyclopentadienyl)silane 1,1-diphenyl-3-(diphenylmethyl)allyl titanium (III).

5. A process for preparing a complex as claimed in claim 1, comprising contacting a titanium complex corresponding to the formula:

wherein: Cp''', Z, Y, and L''' are as defined in claim 1;

M* is titanium in the +4 oxidation state; and

X is halide or $C_{1-10}$ hydrocarbyloxide, with a reducing agent in a diluent at a temperature from 0° to 200° C. to form the complex.

* * * * *